US012344863B2

(12) United States Patent
Yoon et al.

(10) Patent No.: US 12,344,863 B2
(45) Date of Patent: Jul. 1, 2025

(54) METHOD OF PRODUCING STEM CELL-DERIVED ENDOTHELIAL CELLS AND USES THEREOF

(71) Applicants: Emory University, Atlanta, GA (US); The UAB Research Foundation, Birmingham, AL (US); Industry-Academic Cooperation Foundation, Yonsei University, Seoul (KR)

(72) Inventors: Young-Sup Yoon, Atlanta, GA (US); Shin-Jeong Lee, Decatur, GA (US); Ho-Wook Jun, Hoover, AL (US)

(73) Assignees: EMORY UNIVERSITY, Atlanta, GA (US); THE UAB RESEARCH FOUNDATION, Birmingham, AL (US); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 327 days.

(21) Appl. No.: 15/805,894

(22) Filed: Nov. 7, 2017

(65) Prior Publication Data
US 2018/0127713 A1 May 10, 2018

Related U.S. Application Data

(60) Provisional application No. 62/418,636, filed on Nov. 7, 2016.

(51) Int. Cl.
| C12N 5/071 | (2010.01) |
| A61K 35/44 | (2015.01) |
| A61K 47/42 | (2017.01) |
| A61P 9/10 | (2006.01) |

(52) U.S. Cl.
CPC .............. *C12N 5/069* (2013.01); *A61K 35/44* (2013.01); *A61K 47/42* (2013.01); *A61P 9/10* (2018.01); *C12N 2501/42* (2013.01); *C12N 2501/727* (2013.01); *C12N 2506/02* (2013.01); *C12N 2533/54* (2013.01)

(58) Field of Classification Search
CPC ................................ A61K 35/44; C12N 5/069
See application file for complete search history.

(56) References Cited

U.S. PATENT DOCUMENTS

| 8,735,354 | B2 | 5/2014 | Jun | |
| 9,506,037 | B2 | 11/2016 | Gerecht | |
| 2004/0018961 | A1 | 1/2004 | Stupp | |
| 2009/0104159 | A1* | 4/2009 | Prosper | C12N 5/069 424/93.7 |
| 2014/0273220 | A1* | 9/2014 | Gerecht | C12N 5/069 435/377 |
| 2014/0287498 | A1* | 9/2014 | Palecek | C12N 5/069 435/366 |
| 2014/0315305 | A1* | 10/2014 | Shimmura | A61P 27/02 435/377 |
| 2015/0335685 | A1 | 11/2015 | Yoon | |
| 2016/0244719 | A1* | 8/2016 | Thomson | C12N 5/0031 |
| 2018/0030410 | A1* | 2/2018 | Loh | C12N 5/0657 |
| 2018/0216063 | A1* | 8/2018 | Gerecht | C12N 5/069 |

OTHER PUBLICATIONS

Sahara et al., "Manipulation of a VEGF-Notch signaling circuit drives formation of functional vascular endothelial progenitors from human pluripotent stem cells", Cell Research, 2014, vol. 24, pp. 820-841. (Year: 2014).*
Sriram et al., "Efficient differentiation of human embryonic stem cells to arterial and venous endothelial cells under feeder- and serum-free conditions", Stem Cell Research & Therapy, Dec. 2015, 6:261, pp. 1-17. (Year: 2015).*
Aranguren et al., "In vitro and in vivo arterial differentiation of human multipotent adult progenitor cells", Blood, 2007, vol. 109, No. 6, pp. 2634-2642. (Year: 2007).*
Lee et al., "Enhanced Therapeutic and Long-Term Dynamic Vascularization Effects of Human Pluripotent Stem Cell-Derived Endothelial Cells Encapsulated in a Nanomatrix Gel", Circulation, originally published online Sep. 29, 2017, vol. 136, pp. 1939-1954, pp. 1-33/53, plus supplement pp. 34-53/53 (Year: 2017).*
Nieto et al., "Heparin Modulates the Mitogenic Activity of Fibroblast Growth Factor by Inducing Dimerization of its Receptor. A 3D View by using NMR." ChemBioChem, 2013, vol. 14, pp. 1732-1744. (Year: 2013).*
Karnieli et al., "A consensus introduction to serum replacements and serum-free media for cellular therapies", Cytotherapy, 2017; 19: 155-169. (Year: 2017).*

(Continued)

*Primary Examiner* — Laura Schuberg
(74) *Attorney, Agent, or Firm* — Kilpatrick Townsend & Stockton LLP

(57) ABSTRACT

This disclosure relates to methods of generating endothelial cells derived from stem cells. In certain embodiments, the cells are useful for inducing vasculature in muscles and cardiac tissue. In certain embodiments, the disclosure relates to methods of transforming pluripotent or multipotent stem cells, such as embryonic or induced pluripotent stem cells, into endothelial cells derived therefrom using a GSK3 inhibitor and/or delta like canonical notch ligand 4 (DLL4).

17 Claims, 7 Drawing Sheets

Specification includes a Sequence Listing.

(56) References Cited

OTHER PUBLICATIONS

Liu et al., "Regulation of Notch1 and Dll4 by Vascular Endothelial Growth Factor in Arterial Endothelial Cells: Implications for Modulating Arteriogenesis and Angiogenesis", Molecular and Cellular Biology, 2003, vol. 23, No. 1, p. 14-25. (Year: 2003).*
Anderson et al. Modulating the Gelation Properties of Self-Assembling Peptide Amphiphiles, ACS Nano. 2009, 3(11): 3447-3454.
Andukuri et al. Enhanced Human Endothelial Progenitor Cell Adhesion and Differentiation by a Bioinspired Multifunctional Nanomatrix, Tissue Eng Part C Methods. 2013, 19(5):375-85.
Ban et al. Engineered Cell Therapy With Embryonic Stem Cell-Derived Cardiomyocytes Encapsulated in Injectable Nanomatrix Gel Enhanced Engraftment and Promoted Cardiac Repair in Experimental Myocardial Infarction, Circulation, 2013, 128, A18111.
Ban et al. Cell Therapy with Embryonic Stem Cell-Derived Cardiomyocytes Encapsulated in Injectable Nanomatrix Gel Enhances Cell Engraftment and Promotes Cardiac Repair, ACS Nano. 2014, 8(10):10815-25.
Bao et al. Chemically-defined albumin-free differentiation of human pluripotent stem cells to endothelial progenitor cells, Stem Cell Res. 2015, 15(1): 122-129.
Cui et al. Self-Assembly of Peptide Amphiphiles: From Molecules to Nanostructures to Biomaterials, Biopolymers. 2010, 94(1): 1-18.
Jalil et al. Endothelial cells derived from human iPSCs increase capillary density and improve perfusion in a mouse model of peripheral arterial disease, Arterioscler Thromb Vasc Biol. 2011, 1(11): e72-e79.
Kim et al. Self-Assembling Peptide Amphiphile-Based Nanofiber Gel for Bioresponsive Cisplatin Delivery, Mol Pharm, 2009, 6(3): 978-985.
Lee et al. Enhanced Therapeutic and Long-Term Dynamic Vascularization Effects of Human Pluripotent Stem Cell-Derived Endothelial Cells Encapsulated in a Nanomatrix Gel, Circulation, 2017, 136:1939-1954.
Li et al. Functional and Transcriptional Characterization of Human Embryonic Stem Cell-Derived Endothelial Cells for Treatment of Myocardial Infarction, PLoS One, 2009, 4(12): e8443.
Lian et al. Efficient Differentiation of Human Pluripotent Stem Cells to Endothelial Progenitors via Small-Molecule Activation of WNT Signaling, Stem Cell Reports. 2014, 3(5): 804-816.
Tong et al. Application of biomaterials to advance induced pluripotent stem cell research and therapy, EMBO J. 2015, 34(8):987-1008.
Tongers et al. RGDS-Epitope Presenting Peptide Amphiphile Nanofibers Enhance Regenerative Potency of Cell-based Strategies in Ischemic Tissue, Circulation. 2008, 118:S_509.
Webber et al., Development of Bioactive Peptide Amphiphiles for Therapeutic Cell Delivery, Acta Biomater. 2010, 6(1): 3-11.
Yanamandala et al. Overcoming the Roadblocks to Cardiac Cell Therapy Using Tissue Engineering, J Am Coll Cardiol, 2017, 70:766-75.
Jin et al. Vascular nitric oxide: formation and function, Journal of Blood Medicine 2010, 1 147-162.
Corning Matrigel Matrix, available at https://www.corning.com/worldwide/en/products/life-sciences/products/surfaces/matrigel-matrix.html, 2020.
Lian et al., Efficient Differentiation of Human Pluripotent Stem Cells to Endothelial Progenitors via Small-Molecule Activation of WNT Signaling, Stem Cell Reports, 2014.vol. 3, 804-816, Supplemental Information.
Offord, Ku Leuven Investigates Whether Stem Cell Scientist Falsified Data, The Scientist, 2019, available at https://www.the-scientist.com/news-opinion/ku-leuven-investigates-whether-stem-cell-scientist-falsified-data-66835.
WTHR, Stem-cell study used falsified data, available at https://www.wthr.com/article/news/local/stem-cell-study-used-falsified-data/531-8d582174-6617-47a2-8369-37c0c55e3117.

* cited by examiner

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial
<220> FEATURE:
<223> OTHER INFORMATION: Synthetic

<400> SEQUENCE: 1

Gly Thr Ala Gly Leu Ile Gly Gln Arg Gly Asp Ser
1               5                   10

<210> SEQ ID NO 2
<211> LENGTH: 8
<212> TYPE: PRT
<213> ORGANISM: Artificial
<220> FEATURE:
<223> OTHER INFORMATION: Synthetic

<400> SEQUENCE: 2

Gly Thr Ala Gly Leu Ile Gly Gln
1               5

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Gly Thr Ala Gly Leu Ile Gly Gln Ser
1               5

<210> SEQ ID NO 4
<211> LENGTH: 11
<212> TYPE: PRT
<213> ORGANISM: Artificial
<220> FEATURE:
<223> OTHER INFORMATION: Synthetic

<400> SEQUENCE: 4

Gly Thr Ala Gly Leu Ile Gly Lys Lys Lys Lys
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic

<400> SEQUENCE: 5

Gly Thr Ala Gly Leu Ile Gly Lys Lys Lys Lys Lys
1               5                   10

<210> SEQ ID NO 6
<211> LENGTH: 13
<212> TYPE: PRT
```

```
<213> ORGANISM: Artificial
<220> FEATURE:
<223> OTHER INFORMATION: Synthetic

<400> SEQUENCE: 6

Gly Thr Ala Gly Leu Ile Gly Lys Lys Lys Lys Lys
1               5                   10
```

METHOD OF PRODUCING STEM CELL-DERIVED ENDOTHELIAL CELLS AND USES THEREOF

CROSS-REFERENCE TO RELATED APPLICATIONS

This application claims the benefit of priority to U.S. Provisional Application No. 62/418,636 filed Nov. 7, 2016. The entirety of this application is hereby incorporated by reference for all purposes.

STATEMENT REGARDING FEDERALLY FUNDED RESEARCH

This invention was made with government support under DK094346, DK108245, HL127759, and HL129511 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 16145US_ST25.txt. The text file is 2 KB, was created on Nov. 7, 2017, and is being submitted electronically via EFS-Web.

BACKGROUND

Ischemic and cardiovascular diseases are a common cause of mortality. As the loss of vascular supply is a main pathophysiologic feature of these diseases, therapies restoring this fundamental deficit should target growth of blood vessels, for which endothelial cells (ECs) play an important role. Human stem cells, or human pluripotent stem cells (hPSCs), have emerged as promising candidates for vascular regeneration therapy because they have the capacity to differentiate into ECs. However, low survival of transplanted cells in ischemic tissues poses a barrier for cell therapy. In addition, tumor formation is commonly observed. Thus, there is a need to identify improved methods of generating cells capable of forming vasculature.

Li et al report the characterization of human embryonic stem cell-derived endothelial cells for treatment of myocardial infarction. PLoS ONE, 2009, 4(12): e8443.

Rufaihah et al. report endothelial cells derived from human iPSCs increase capillary density and improve perfusion in a mouse model of peripheral arterial disease. Arterioscler Thromb Vasc Biol. 2011, 31:e72-79.

Bao et al. report chemically-defined albumin-free differentiation of human pluripotent stem cells to endothelial progenitor cells. Stem Cell Res. 2015, 15:122-129. See also Lian et al. Efficient Differentiation of Human Pluripotent Stem Cells to Endothelial Progenitors via Small-Molecule Activation of WNT Signaling. Stem Cell Reports. 2014, 3:804-16.

Yoon et al. report engineered stem cell therapy for cardiac repair. See also US Application Publication No. 2015-0335685

References cited herein are not an admission of prior art.

SUMMARY

This disclosure relates to methods of generating endothelial cells derived from stem cells. In certain embodiments, the cells are useful for inducing vasculature in muscles and cardiac tissue. In certain embodiments, the disclosure relates to methods of transforming pluripotent or multipotent stem cells, such as embryonic or induced pluripotent stem cells, into endothelial cells derived therefrom using a GSK3 inhibitor and/or delta like canonical notch ligand 4 (DLL4).

In certain embodiments, the disclosure contemplates methods of producing stem cell-derived endothelial cells comprising: culturing stem cells with a GSK3 inhibitor under conditions such that the stem cells express increased Branchyury (T) and vascular endothelial growth factor receptor 2 (KDR) transcripts providing mesodermally differentiated cells; and culturing the mesodermally differentiated stem cells with delta like canonical notch ligand 4 (DLL4) under conditions such that the mesodermally differentiated stem cells express increased one or more or all of PECAM1, CDH5, and VWF transcripts providing stem cell-derived endothelial cells.

In certain embodiments, the method further comprises purifying the stem cell-derived endothelial cells by selecting cells that express an endothelial marker such as CDH5. In certain embodiments, culturing stem cells with a GSK3 inhibitor is on a surface comprising or coated with collagen. In certain embodiments, culturing is for not more than 3 or 4 days.

In certain embodiments, the disclosure relates to an autologous cell therapy comprising isolating cells from a subject, reprogramming the isolated cells into induced pluripotent stem cells, transforming the induced pluripotent stem cells into autologous stem cell-derived endothelial cells using methods disclosed herein, and administering or transplanting the autologous stem cell-derived endothelial cells into the subject in need thereof to treat an ischemic or cardiac disease or condition. In certain embodiments, the disclosure contemplates that the isolated cells are mesenchymal stem cells or hematopoietic stem cells, e.g. isolated from bone marrow or peripheral blood.

In certain embodiments, the disclosure contemplates a pharmaceutical composition comprising pluripotent stem cell-derived endothelial cells made by the processes disclosed herein and a pharmaceutically acceptable excipient.

In certain embodiments, the disclosure contemplates methods of treating or preventing an ischemic or cardiac disease or condition comprising administering an effective amount of a pharmaceutical composition comprising pluripotent stem cell-derived endothelial cells made by the processes disclosed herein to a subject in need thereof. In certain embodiments, the ischemic disease or condition is peripheral artery disease, limb ischemia, coronary artery disease, angina, a heart attack, stroke, transient ischemic attacks, or mesenteric ischemia.

In certain embodiments, the disclosure contemplates compositions comprising stem cell-derived endothelial cells made by the processes disclosed herein and a peptide amphiphile. In certain embodiments, the peptide amphiphile comprises a cell adhesive peptide sequence and a protease degradable sequence linked to a hydrocarbon.

In certain embodiments, this disclosure contemplates methods of inducing the vascularization comprising implanting an effective amount of a composition disclosed herein in the muscle or cardiac tissue of a subject in need thereof.

In certain embodiments, the disclosure contemplates methods of inducing the vascularization comprising: providing a gel comprising stem cell-derived endothelial cells made by the process disclosed herein and a peptide amphiphile; and implanting an effective amount of the gel in the muscle or heart of a subject in need thereof.

In certain embodiments, the disclosure relates to a composition comprised of peptide amphiphiles and stem cell-derived endothelial cells, and administering such a composition to a subject for use in the treatment of an ischemic or cardiovascular disease or condition. In certain embodiments, the peptide amphiphiles comprise a cell adhesive sequence and a metalloprotease degradable sequence.

In certain embodiments, the disclosure relates to compositions comprising a) a peptide amphiphile comprising a cell adhesive peptide sequence and a protease degradable sequence linked to a hydrocarbon; and b) stem cell-derived endothelial cells disclosed herein. In certain embodiments, the stem cell-derived endothelial cells made by the process of culturing isolated cells, e.g., stem cells or induced pluripotent stem cells using methods disclosed herein.

DETAILED DISCUSSION

Figure 1A:
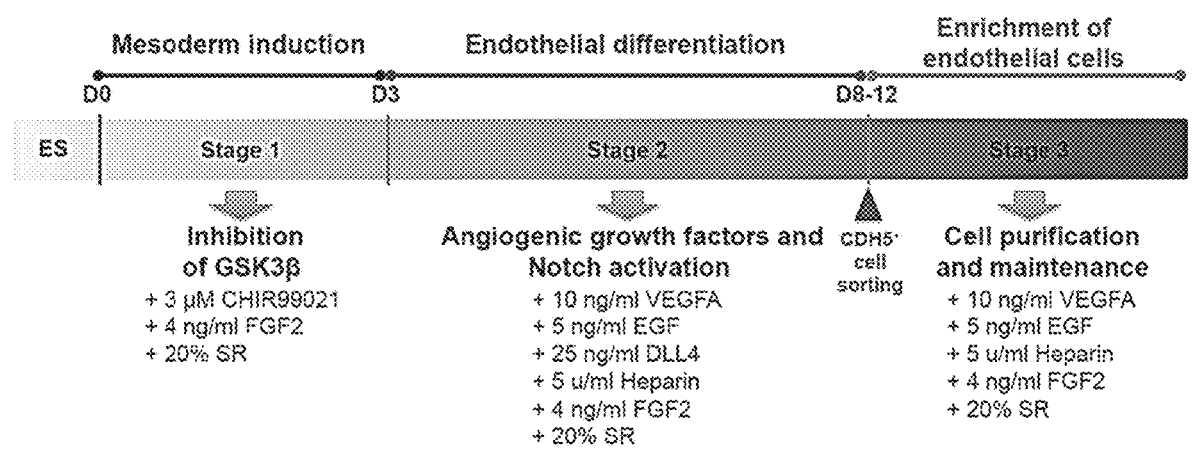
FIG. 1A illustrates differentiation of hPSCs into ECs. (a) Three stages of differentiation from hPSCs into ECs. Stage 1: Mesoderm induction. Stage 2: Endothelial differentiation. Stage 3: EC enrichment.
Figure 1B:
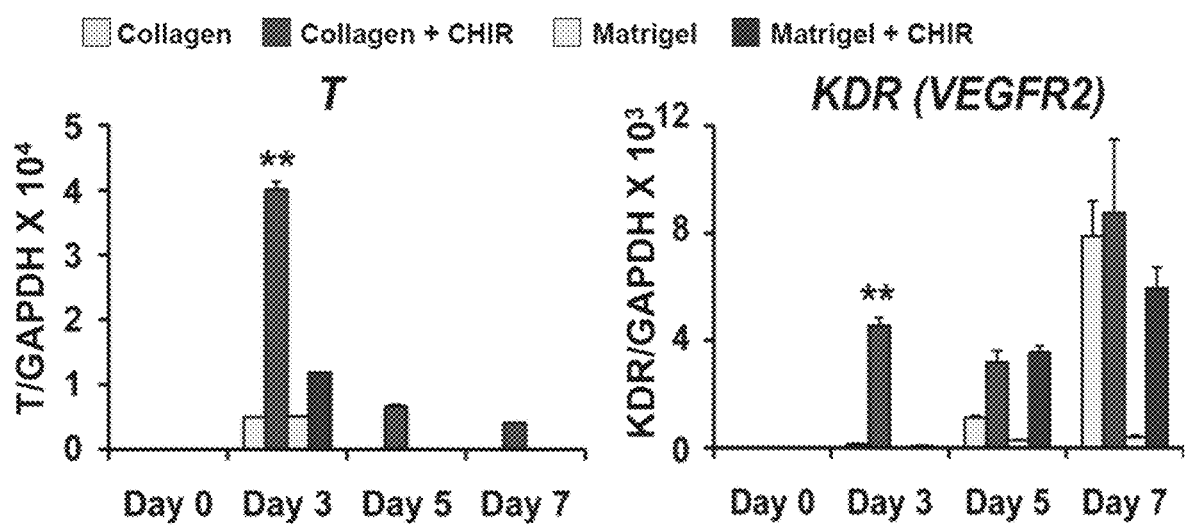
FIG. 1B shows data indicating the differentiation of hPSCs into mesodermal lineages with mRNA increased expression of T, KDR using collagen a coating and CHIR99021 treatment for 3 days.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

"Subject" refers any animal, preferably a human patient, livestock, or domestic pet.

The terms "protein" and "polypeptide" refer to compounds comprising amino acids joined via peptide bonds and are used interchangeably. Amino acids may be naturally or non-naturally occurring.

A "variant" refers to a chemically similar sequence because of amino acid changes or chemical derivative thereof. In certain embodiments, a variant contains one, two, or more amino acid deletions or substitutions. In certain embodiments, the substitutions are conserved substitutions. In certain embodiments, a variant contains one, two, or ten or more an amino acid additions. The variant may be substituted with one or more chemical substituents.

One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on). As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

The term "delta like canonical notch ligand 4 (DLL4)" refers to a polypeptide comprising a mature human or mammalian peptide sequence encoded by a DLL4 gene. See, e.g., human NCBI Reference Sequence: NP_061947.1.

The term "collagen" refers to the fibril forming collagen proteins comprising tripeptide repeats of the amino acids Glycine-Proline-Hydroxyproline. Proline and hydroxyproline may be substituted with other amino acids; however, proline and hydroxyproline are the most abundant amino acids in those positions. Collagen further forms a coiled structure that leads to the formation of fibrils.

The term "mesenchymal stromal cells" refers to the subpopulation of fibroblast or fibroblast-like nonhematopoietic cells with properties of plastic adherence and capable of in vitro differentiation into cells of mesodermal origin which may be derived from bone marrow, adipose tissue, umbilical cord (Wharton's jelly), umbilical cord perivascular cells, umbilical cord blood, amniotic fluid, placenta, skin, dental pulp, breast milk, and synovial membrane, e.g., fibroblasts or fibroblast-like cells with a clonogenic capacity that can differentiate into several cells of mesodermal origin, such as adipocytes, osteoblasts, chondrocytes, skeletal myocytes, or visceral stromal cells. The term, "mesenchymal stem cells" refers to the cultured (self-renewed) progeny of primary mesenchymal stromal cell populations. Mesenchymal stromal/stem cells (MSCs) refers to mesenchymal stromal and/or mesenchymal stem cells.

Bone marrow derived mesenchymal stromal cells are typically expanded ex vivo from bone marrow aspirates to confluence. Certain mesenchymal stromal/stem cells (MSCs) share a similar set of core markers and properties. Certain mesenchymal stromal/stem cells (MSCs) may be defined as positive for CD105, CD73, and CD90 and negative for CD45, CD34, CD14 or CD11b, CD79α or CD19, and HLA-DR surface markers, and have the ability to adhere to plastic. See Dominici et al. Minimal criteria for defining multipotent mesenchymal stromal cells. The International Society for Cellular Therapy position statement. Cytotherapy. 2006, 8(4):315-7.

As used herein, "selecting cells that express" a specific protein refers to purify the cells from other cells that do not express or express less of the protein. A typical method of selecting proteins that are expressed on the outside of the cell membrane is to provide a specific binding agent, such as a primary antibody, and further trap the primarily antibody bound to the cells surface marker using a secondary antibody that is conjugated to magnetic beads. The magnetic beads can be captured by a magnetic field and separated from the rest of a solution. In another method, secondary antibodies contains a fluorescent marker and the cells can be separated using fluorescence activated cell sorting.

In another method, cells that express a protein are isolated using molecular beacon based sorting technique. See Ban et al., Circulation, 2013, 128: 1897-1909 and U.S. patent application Ser. No. 14/211,430. Molecular beacon (MB) technology is a method of sorting cells based on mRNA sequences. MBs are 20-30 base pair (bp) oligonucleotide probes with a fluorophore conjugated to the 5' end and a quencher at the 3' end. (Heyduk T & Heyduk E, 2002 Nat Biotech, 20:171-176). MBs are designed with 4-7 bps at the 5' end which are complementary to the bps at the 3' end. This self-complementary configuration induces the oligonucleotides to form a stem-loop (hairpin) structure so that the fluorophore and the quencher are within close proximity (<7 nm) and fluorescence is quenched. Hybridization of the MBs with the target mRNA opens the hairpin structure and physically separates the fluorophore from the quencher, allowing a fluorescence signal to be emitted upon excitation. (Tsourkas et al., 2002, Nucleic acids research, 30:4208-4215). Molecular beacons that target the cell specific mRNA are typically made up of an oligonucleotide sequence of that is complementary to the specific target mRNA associates with the protein of interest. MB technology may be used to separate and purify specific cell populations for example specific subpopulations of cells using fluorescent activated cell sorting.

The term "fluorescence-activated cell sorting" or "FACS" refers to a method of sorting a mixture of cells into two or more areas, typically one cell at a time, based upon the fluorescent characteristics of each cell. It is typically accomplished by applying an electrical charge and separating by movement through an electrostatic field. Fluorescent antibodies with epitopes to cell surface markers can be mixed with cells to mark the cells or cells can be transfected with fluorescent probes or molecular beacons that bind to mRNA. Typically, in FACS, a vibrating mechanism causes a stream of cells to break into individual droplets. Just prior to droplet formation, cells in a fluid pass through an area for measuring fluorescence of the cell. An electrical charging mechanism is configured at the point where the stream breaks into droplets. Based on the fluorescence intensity measurement, a respective electrical charge is imposed on the droplet as it breaks from the stream. The charged droplets then move through an electrostatic deflection system that diverts droplets into areas based upon their relative charge. In some systems, the charge is applied directly to the stream, and the droplet breaking off retains charge of the same sign as the stream. In other systems, a charge is provided on a conduit inducing an opposite charge on the droplet.

As used herein a "growth medium" or "media" refers to a composition that contains components, such as vitamins, amino acids, inorganic salts, a buffer, and a fuel, e.g., acetate, succinate, and/or a saccharide, that support the growth and maintenance of cell lines. Components in the growth medium may be derived from blood serum or the growth medium may be serum-free. The growth medium may optionally be supplemented with albumin, lipids, insulin and/or zinc, transferrin or iron, selenium, ascorbic acid, and an antioxidant such as glutathione, 2-mercaptoethanol or 1-thioglycerol.

Human Pluripotent Stem Cell-Derived Endothelial Cells Differentiated in a Fully Defined System and Encapsulated in a Nanomatrix Gel Experiments disclosed herein addressed two major roadblocks for cardiovascular cell therapy: 1) generation of clinically compatible, high-purity, therapeutically effective, and safe hPSC-derived ECs, and 2) enabling long-term survival of hPSC-ECs in ischemic tissue via encapsulation within the nanomatrix gel, thus enhancing their therapeutic effects. Long-term in vivo behavior of hPSC-ECs in ischemic tissues provided sustained and dynamic incorporation of engrafted hPSC-ECs into the host vessels and a guiding role of hPSC-ECs for new vessel formation.

Employing two molecules, CHIR99021 and DLL4, and sorting with CDH5, a highly efficient EC differentiation system is established. The purified hPSC CDH5+ cells produced nitric oxide, an important marker for functional ECs. The resultant hPSC-ECs have unique characteristics that favor clinical translation. The protocol employs fully defined conditions and showed no cell line variability among the lines tested. A main advantage of hiPSC technology is its potential for autologous therapy. hPSC-derived ECs generated by the protocol demonstrated proangiogenic potential and direct vessel-forming effects. These dual characteristics have respective benefits, as each contributed to therapeutic neovascularization at different time points. The implanted hPSC-ECs, even encapsulated, did not induce tumorigenic or other side effects during long-term follow-up.

The peptide amphiphile nanomatrix gel dramatically increased survival of hPSC-ECs and induced robust and longstanding vascular regenerative effects. The unique structural and functional characteristics of the nanomatrix gel provide important insight into how encapsulated hPSC-ECs exert therapeutic effects for tissue ischemia. Initially the ECM-mimicking structure incorporating adhesive ligands allows easy adhesion of the nanomatrix gel with host ECM, stabilization of encapsulated hPSC-ECs, and transport of nutrients and growth factors by diffusion, thereby promoting the viability of the encapsulated hPSC-ECs and exerting proangiogenic effects on the host cells during the critical early phase of cell survival.

Degradation of the nanomatrix gel then exposes and allows migration of encapsulated hPSC-ECs into ischemic areas and structural contribution of hPSC-ECs to vessel formation. This vasculogenic effect gradually becomes the main role for vascularization. Long-term retention of hPSC-ECs via the nanomatrix gel allowed one to examine temporal reorganization of engrafted cells and their relation to new vessel formation.

It has been discovered that after several weeks, nanomatrix gel implanted hPSC-ECs cells migrate toward vessels and directly incorporate into vessels. When hPSC-ECs alone were implanted, most cells died within several weeks, so that most effects are paracrine. However, when hPSC-ECs were delivered within the nanomatrix gel, many cells were protected and thus had an opportunity to migrate toward vascular areas later. Second, the proportion of engrafted hPSC-ECs incorporated into the vessels increased steadily over 10 months. Initially, hPSC-ECs were more localized in the perivascular areas; however, during host vessel reorganization and new vessel formation, more hPSC-ECs were incorporated into the vessels. Thus, long-term engraftment is a critical factor for ongoing vasculogenesis by hPSC-ECs.

hPSC-ECs showed a guiding role for vessel growth, which enables multiple cellular incorporation during vessel formation. Even at 10 months, a guiding role and sustained and robust vessel growth was observed, attributed to surviving hPSC-ECs. These data indicate that hPSC-ECs can be useful for clinical therapy for ischemic cardiovascular disease, since most human cardiovascular diseases are chronic and require sustained vessel formation for effective treatment.

Embryonic Stem Cells (ESCs) to Induced Pluripotent SCs

Embryonic stem cells (ESCs) originate from the inner cell mass of mammalian blastocysts which occur 5-7 days after fertilization. ESCs remain undifferentiated indefinitely under defined conditions and differentiate into so-called embryonic bodies when cultivated in vitro. Having pluripotency, they are capable of differentiating into all cells. Adult stem cells have an ability to become more than one cell type but do not have the ability to become any cell type.

Induced pluripotent stem cells (iPSCs) are differentiated cells reprogrammed to return to a pluripotent stage. Reprogrammed fully differentiated cells may be accomplished using genes involved in the maintenance of ESC pluripotency, e.g., Oct3/4, Sox2, c-Myc, and Klf4. The term "induced pluripotent stem cells" refers to cells that are reprogrammed from somatic or adult stems cells to an embryonic stem cell (ESC)-like pluripotent state. See Takahashi et al. Induction of pluripotent stem cells from mouse embryonic and adult fibroblast cultures by defined factors. Cell. 2006, 126(4):663-76. Park et al. report reprogramming of human somatic cells to pluripotency with defined factors. Nature. 2008, 451(7175):141-6. Thus, making iPSCs in cells can typically be accomplished by in trans expression of OCT4, SOX2, KLF4 and c-MYC. Colonies appear and resemble ESCs morphologically. Alternatively, certain multipotent stem cells may require less than all of the four transcripts, e.g., cord blood CD133+ cells require only OCT4 and SOX2 to generate iPSCs. For additional guidance in generating iPSCs, see Gonzalez et al. "Methods of making induced pluripotent stem cells: reprogramming a la carte," Nature Reviews Genetics, 12, 231-242 (April 2011).

Methods of Use

This disclosure relates to methods of generating endothelial cells derived from stem cells such as pluripotent or multipotent stem cells. In certain embodiments, the cells are useful for inducing vasculature in muscles and cardiac tissue. In certain embodiments, the disclosure relates to methods of transforming pluripotent or multipotent stem cells, such as embryonic or induced pluripotent stem cells, into endothelial cells derived therefrom using a GSK3 inhibitor and/or delta like canonical notch ligand 4 (DLL4).

In certain embodiments, the disclosure contemplates methods of culturing stem cells with an GSK3 inhibitor under conditions such that the stem cells express increased Branchyury (T) and vascular endothelial growth factor receptor 2 (KDR) transcripts providing mesodermally differentiated cells.

In certain embodiments, the disclosure contemplates methods of culturing the mesodermally differentiated stem cells or mesodermally isolated stem cells with delta like canonical notch ligand 4 (DLL4) under conditions such that the mesodermally differentiated stem cells or mesodermally isolated stem cells express increased PECAM1, CDH5, and VWF transcripts providing stem cell-derived endothelial cells.

In certain embodiments, the disclosure contemplates methods of producing stem cell-derived endothelial cells comprising: culturing stem cells with a GSK3 inhibitor under conditions such that the stem cells express increased Branchyury (T) and vascular endothelial growth factor receptor 2 (KDR) transcripts providing mesodermally differentiated cells; and culturing the mesodermally differentiated stem cells with delta like canonical notch ligand 4 (DLL4) under conditions such that the mesodermally differentiated stem cells express increased one or more or all of PECAM1, CDH5, and VWF transcripts providing stem cell-derived endothelial cells.

In certain embodiments, the method further comprises purifying the stem cell-derived endothelial cells by selecting cells that express an endothelial marker such as CDH5. In certain embodiments, culturing stem cells with a GSK3 inhibitor is on a surface comprising or coated with collagen. In certain embodiments, culturing is for not more than 3 or 4 days.

In certain embodiments, the stem cells are embryonic stem cells, human embryonic stem cells, induced pluripotent stem cells, human induced pluripotent stem cells, adult stem cells, adult endothelial stem cells, umbilical cord blood stem cells, or an embryoid body.

In certain embodiments, the disclosure contemplates methods of treating or preventing an ischemic disease or condition comprising administering an effective amount of a pharmaceutical composition comprising stem cell-derived endothelial cells made by the processes disclosed herein to a subject in need thereof. In certain embodiments, the ischemic disease or condition is peripheral artery disease, limb ischemia, coronary artery disease, angina, a heart attack, stroke, transient ischemic attacks, or mesenteric ischemia.

In certain embodiments, the disclosure relates to an autologous cell therapy comprising isolating cells from a subject, reprogramming the isolated cells into induced pluripotent stem cells, transforming the induced pluripotent stem cells into autologous stem cell-derived endothelial cells using methods disclosed herein, and administering or transplanting the autologous stem cell-derived endothelial cells into the subject in need thereof to treat an ischemic or cardiac disease or condition. In certain embodiments, the disclosure contemplates that the isolated cells are mesenchymal stem cells or hematopoietic stem cells, e.g. isolated from bone marrow or peripheral blood.

In certain embodiments, the stem cells are embryonic stem cells, human embryonic stem cells, induced pluripotent stem cells, human induced pluripotent stem cells, adult stem cells, adult endothelial stem cells, umbilical cord blood stem cells, or an embryoid body.

In certain embodiments, the disclosure relates to methods of transforming stem cells into stem cell derived endothelial cells using delta like canonical notch ligand 4 (DLL4) using methods disclosed herein. In certain embodiments, the stem cells are mesenchymal stem cells or hematopoietic stem cells, such as cells in peripheral blood or bone marrow purified by selecting cells that express CD31 or CD34.

In certain embodiments, the GSK3 inhibitor is selected from:
6-[[2-[[4-(2, 4-dichlorophenyl)-5-(5-methyl-1H-imidazol-2-yl)-2-pyrimidinyl]amino]ethyl]amino]-3-pyridinecarbonitrile (CHIR99021);
N-6-[2-[[4-(2,4-Dichlorophenyl)-5-(1H-imidazol-1-yl)-2-pyrimidinyl]amino]ethyl]-3-nitro-2,6-pyridinediamine (CHIR-98014);
3-(1,3-Dihydro-3-oxo-2H-indol-2-ylidene)-1,3-dihydro-2H-indol-2-one (Indirubin);
6-bromoindirubin-3'-oxime (BIO);
6-bromoindirubin-3'-acetoxime (BIO-acetoxime);
3-(2,4-Dichlorophenyl)-4-(1-methyl-1H-indol-3-yl)-1H-pyrrole-2,5-dione (SB21676);
3-[6-(3-Aminophenyl)-7H-pyrrolo[2,3-d]pyrimidin-4-yloxy]phenol (TWS119);
4-benzyl-2-(naphthalen-1-yl)-[1,2,4]thiadiazolidine-3,5-dione (Tideglusib);
3-[(3-Chloro-4-hydroxyphenyl)-amino]-4-(2-nitrophenyl)-1H-pyrrol-2,5-dione (SB415286);
3-amino-6-[4-[(4-methyl-1-piperazinyl)sulfonyl]phenyl]-N-3-pyridinyl-2-pyrazinecarboxamide (AZD2858);
2-hydroxy-3-[5-[(morpholin-4-yl)methyl]pyridin-2-yl]-1H-indole-5-carbonitrile (AZD1080);
N-(4-methoxybenzyl)-N'-(5-nitro-1,3-thiazol-2-yl)urea (AR-A014418);
3-[9-fluoro-1,2,3,4-tetrahydro-2-(1-piperidinylcarbonyl) pyrrolo[3,2,1-jk][1,4]benzodiazepin-7-yl]-4-imidazo[1,2-a]pyridin-3-yl-1h-pyrrole-2,5-dione (LY2090314); and
3-(4-fluorophenylethylamino)-1-methyl-4-(2-methyl-1H-indol-3-yl)-1H-pyrrole-2,5-dione (IM-12) or salts thereof.

In certain embodiments, culturing the mesodermally differentiated stem cells with DLL4 providing, stem cell-derived endothelial cells is in the absence or presence of BMP-4 and/or Acitivin A and/or bFGF.

In certain embodiments, culturing the mesodermally differentiated stem cells with delta like canonical notch ligand 4 (DLL4) is in the presence or absence of an inhibitor of TGF-β signaling pathway such as 4-[4-(1,3-Benzodioxol-5-yl)-5-(2-pyridinyl)-1H-imidazol-2-yl]-benzamide (SB431542).

In certain embodiments, the disclosure contemplates compositions comprising pluripotent stem cell-derived endothelial cells made by the processes disclosed herein and a peptide amphiphile. In certain embodiments, the peptide amphiphile comprises a cell adhesive peptide sequence and a protease degradable sequence linked to a hydrocarbon.

In certain embodiments, this disclosure contemplates methods of inducing the vascularization comprising implanting an effective amount of a composition disclosed herein in the muscle of a subject in need thereof.

In certain embodiments, the disclosure contemplates methods of inducing the vascularization comprising: providing a gel comprising pluripotent stem cell-derived endothelial cells made by the process disclosed herein and a peptide amphiphile; and implanting an effective amount of the gel in the muscle of a subject in need thereof.

In certain embodiments, the disclosure relates to a composition comprised of peptide amphiphiles and pluripotent stem cell-derived endothelial cells, and administering such a composition to a subject for use in the treatment of an ischemic or cardiovascular disease or condition. In certain embodiments, the peptide amphiphiles comprise a cell adhesive sequence and a metalloprotease degradable sequence.

In certain embodiments, the disclosure relates to compositions comprising a) a peptide amphiphile comprising a cell adhesive peptide sequence and a protease degradable sequence linked to a hydrocarbon; and b) pluripotent stem cell-derived endothelial cells disclosed herein. In certain embodiments, the pluripotent stem cell-derived endothelial cells made by the process of culturing isolated cells, e.g., stem cells or induced pluripotent cells using methods disclosed herein.

In certain embodiments, the disclosure relates to a method of growing stem cell derived endothelial cells in culture, wherein said culture is used for screening of drugs for potential treatment of an ischemic or cardiac condition. In certain embodiments, the disclosure relates to a method of growing derived endothelial cells in culture, wherein said culture is used for screening of drugs for potential treatment of an ischemic or cardiac condition.

A "cardiac condition" is a state of the heart that can be identified by symptoms or other identifying factors as diverging from a healthy or a normal state. The term "cardiac condition" includes disorders, syndromes, diseases, and injuries that affect the heart. Cardiac conditions include, but are not limited to, cardiac failure, for example, congestive heart failure; ischemic conditions, for example, myocardial infarction; hypertensive conditions; congenital conditions; infectious conditions, for example, endocarditis; and coronary artery disease. Cardiac conditions also include myocardial diseases, for example, myocarditis, cardiomyopathy, and fibrosis; pericardial diseases, for example, pericarditis; and endocardial and valvular diseases, for example, stenosis and prolapse.

Peptide Amphiphiles

The term "peptide amphiphile" as used herein refers to a peptide-based molecule that comprises both a hydrophobic domain and hydrophilic domain. In certain embodiments, the peptide amphiphile has the capability to self-assemble into a three-dimensional network. In certain embodiments, the peptide amphiphiles can self-assemble into a three-dimensional structure that closely mimics the extracellular matrix that surrounds cells in native tissues. In certain embodiments, the peptide amphiphile can provide a protective microenvironment while simultaneously promoting localized extracellular matrix formation and intercellular connections in transplanted cells. In certain embodiments, the peptide amphiphile can promote vascular generation.

In certain embodiments, the hydrophobic domain is comprised of a peptide chain wherein the amino acids that comprise said peptide chain have hydrophobic properties. In certain embodiments, the hydrophobic domain is comprised of a hydrocarbon chain. In certain embodiments, the hydrocarbon chain contains between 2 and 20 carbon molecules. In the preferred embodiment, the hydrocarbon chain contains 16-18 carbon molecules or derivatives.

In certain embodiments, the hydrophilic domain is comprised of a peptide chain wherein the amino acids that comprise said peptide chain have hydrophilic properties. In certain embodiments, the hydrophilic peptide chain contains a cell adhesion ligand binding sequence.

In certain embodiments, the peptide amphiphile comprises a second hydrophilic peptide sequence. In certain embodiments the second hydrophilic peptide sequence, is an enzyme mediated degradable site. In certain embodiments, the second hydrophilic peptide sequence is a matrix metalloprotease-2 (MMP-2) degradable sequence. In certain embodiments, the second hydrophilic peptide sequence has the amino acid sequence GTAGLIGQ (SEQ ID NO: 2). In certain embodiments, the second hydrophilic peptide sequence allows progressive degradation of the peptide amphiphile scaffold and replacement by natural extracellular matrix produced by the cells.

In certain embodiments, the disclosure relates to a composition comprising a peptide amphiphile comprising a cell adhesive sequence and a second sequence, wherein the second sequence comprise between 5 and 20 amino acids wherein more than 50 percent of the amino acids are glycine or a hydrophilic amino acid; wherein the second sequence is linked to a hydrocarbon with a carbon chain of greater than 6; and derived endothelial cell disclosed herein. In certain embodiments, the peptide amphiphile is alkyl-CONH-GTAGLIGQ-RGDS (SEQ ID NO: 1) or variants thereof.

In certain embodiments, the disclosure relates to compositions comprising a cell adhesive sequence that is an integrin binding cell adhesive ligand. In certain embodiments, the cell adhesive sequence is RGD. In certain embodiments, the second sequence is GTAGLIGQ (SEQ ID NO: 2). In certain embodiments, the hydrocarbon contains an 8 to 22 carbon chain.

In certain embodiments, the peptide amphiphile is alkyl-CONH-GTAGLIG (SEQ ID NO: 2)-poly-lysine, e.g., alkyl-CONH-GTAGLIG-KKKK (SEQ ID NO: 4), alkyl-CONH-GTAGLIG-KKKKK (SEQ ID NO: 5), or alkyl-CONH-GTAGLIG-KKKKKK(SEQ ID NO: 6).

In certain embodiments, the compositions comprise the amphiphile peptides as a combination of is alkyl-CONH-GTAGLIGQ-RGDS(SEQ ID NO: 1) and alkyl-CONH-GTAGLIG(SEQ ID NO: 2)-poly-lysine.

In certain embodiments, alkyl is CH3(CH2)n-, e.g, CH3(CH2)14-, wherein n is 6 or more, e.g., 6-20.

In certain embodiments, compositions comprising a) a peptide amphiphile comprising a cell adhesive peptide sequence and a protease degradable sequence linked to a hydrocarbon also contains a peptide amphiphile without a cell adhesive peptide sequence. In certain embodiments, the ratio of peptide amphiphiles containing a cell adhesive sequence to peptide amphiphiles without a cell adhesive sequence is between 1:1 to 1:2, or 1:2 to 1:3, or 1:3 to 1:4, or 1:4 to 1:5, or 1:5 to 1:10, or 2:1 to 1:1, or 3:1 to 2:1, or 4:1 to 3:1, or 5:1 to 4:1, or 10:1 to 5:1. In certain embodiments, the peptide amphiphiles are alkyl-CONH-GTAGLIGQ-RGDS (SEQ ID NO: 1) and alkyl-CONH-GTAGLIGQ-S(SEQ ID NO: 3)

Pharmaceutical Compositions

Compositions comprising stem cell derived endothelial cells made by processes disclosed herein having the potential to differentiate into an endothelial cell (e.g., progeny thereof) can be provided systemically or locally for the treatment of a disease characterized by ischemia cell death or loss. In one embodiment, stem cell derived endothelial cells made by processes disclosed herein are provided locally to a tissue. Alternatively, compositions comprising stem cell derived endothelial cells made by processes disclosed herein can be provided indirectly to the tissue of interest, for example, by local administration into a muscle or cardiac tissue. Following transplantation or implantation, the cells may engraft and differentiate into progeny endothelial cells. "Engraft" refers to the process of cellular contact and incorporation into an existing tissue of interest in vivo. Expansion and differentiation agents can be provided prior to, during or after administration to increase production of endothelial cells in vivo.

In certain embodiments, this disclosure relates pharmaceutical compositions comprising stem cell derived endothelial cells made by processes disclosed herein and a pharmaceutically acceptable carrier. Administration can be autologous or heterologous. For example, induced pluripotent stem cells used to make stem cell derived endothelial cells made by processes disclosed herein can be obtained from one subject, and administered to the same subject or a different, compatible subject.

Stem cell derived endothelial cells made by processes disclosed herein can be administered via localized injection, including catheter administration, systemic injection, localized injection, intravenous injection, intramuscular injection, intraneural injection or parenteral administration. When administering a therapeutic composition of the present invention (e.g., a pharmaceutical composition), it will generally be formulated in a unit dosage injectable form (solution, suspension, emulsion).

Compositions can be conveniently provided as sterile gel or liquid preparations, e.g., isotonic aqueous solutions, suspensions, emulsions, dispersions, or viscous compositions, which may be buffered to a selected pH. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the cells utilized in practicing methods disclosed herein in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

The compositions can be isotonic, i.e., they can have the same osmotic pressure as blood and lacrimal fluid. The desired isotonicity of the compositions of this invention may be accomplished using sodium chloride, or other pharmaceutically acceptable agents, such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

A method to potentially increase cell survival when introducing the cells into a subject in need thereof is to incorporate stem cell derived endothelial cells made by processes disclosed herein into a biopolymer or synthetic polymer. Depending on the subject's condition, the site of injection might prove inhospitable for cell seeding and growth because of scarring or other impediments. Examples of biopolymer include, but are not limited to, cells mixed with peptide amphiphiles, fibronectin, fibrin, fibrinogen, thrombin, collagen, proteoglycans and other protein components of the extracellular matrix. This could be constructed with or without included expansion factors, differentiation factors, endothelial cell promoting factors, neurotrophic factors, or angiogenic factors. Additionally, these could be in suspension, but residence time at sites subjected to flow would be nominal. Another alternative is a three-dimensional gel with cells entrapped within the interstices of the cell biopolymer admixture. Again, expansion or differentiation factors could be included with the cells. These could be deployed by injection via various routes described herein.

Stem cell derived endothelial cells made by processes disclosed herein can be cultured, treated with agents and/or administered in the presence of polymer scaffolds. Polymer scaffolds are designed to optimize gas, nutrient, and waste exchange by diffusion. Polymer scaffolds can comprise, for example, a porous, non-woven array of fibers. The polymer scaffold can be shaped to maximize surface area, to allow adequate diffusion of nutrients and growth factors to the cells. Taking these parameters into consideration, one of skill in the art could configure a polymer scaffold having sufficient surface area for the cells to be nourished by diffusion until new blood vessels interdigitate the implanted engineered-tissue using methods known in the art. Polymer scaffolds can comprise a fibrillar structure. The fibers can be round, scalloped, flattened, star-shaped, solitary or entwined with other fibers. Branching fibers can be used, increasing surface area proportionately to volume.

Unless otherwise specified, the term "polymer" includes polymers and monomers that can be polymerized or adhered to form an integral unit. The polymer can be non-biodegradable or biodegradable, typically via hydrolysis or enzymatic cleavage. The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo(ε-caprolactone)diol as switching segment/oligo(p-dioxyanone)diol as physical crosslink. Other suitable polymers can be obtained by reference to The Polymer Handbook, 3rd edition (Wiley, N.Y., 1989).

Factors, including but not limited to nutrients, growth factors, inducers of differentiation or de-differentiation, products of secretion, immunomodulators, cytokines, neurotrophic factors, myogenic factors, angiogenic factors, inhibitors of inflammation, regression factors, hormones, various tissue extracts (e.g. from myocardium or skeletal muscle) or other biologically active compounds can be incorporated into or can be provided in conjunction with the polymer scaffold.

One consideration concerning the therapeutic use of stem cell derived endothelial cells made by processes disclosed herein is the quantity of cells necessary to achieve an optimal effect. In current human studies of autologous mononuclear peripheral blood cells, empirical doses ranging from 1 to $4 \times 10^7$ cells have been used with encouraging results. The methods of the disclosure may require optimization of the amount of cells injected into a tissue of interest. Thus, the quantity of cells to be administered will vary depending on the tissue or the subject being treated. In one embodiment, between $10^4$ to $10^8$, $10^6$ to $10^8$, or $10^5$ to $10^9$ cells are implanted. In other embodiments, $10^5$ to $10^7$ cells are implanted. In still other embodiments, $3 \times 10^7$ stem cells of the invention can be administered to a human subject. The precise determination of an effective dose may be based on factors individual to each patient, including their size, age, sex, weight, and condition. Therefore, dosages are determined empirically using no more than routine by those skilled in the art from this disclosure and the knowledge in the art.

Those skilled in the art can readily determine the percentage of such cells in a population using various well-known methods, such as fluorescence activated cell sorting (FACS). Desirable ranges of purity in mixed populations comprising stem cell derived endothelial cells made by processes disclosed herein are about 85 to about 90%, about 90 to about 95%, and about 95 to about 100%. Purity of stem cell derived endothelial cells made by processes disclosed herein can be determined according to the marker profile within a population. Dosages can be readily adjusted by those skilled in the art (e.g., a decrease in purity may require an increase in dosage).

Agents of the disclosure may be supplied along with additional reagents in a kit. The kits can include instructions for the treatment regime or assay, reagents, equipment (test tubes, reaction vessels, needles, syringes, etc.) and standards for calibrating or conducting the treatment or assay. The instructions provided in a kit according to the disclosure may be directed to suitable operational parameters in the form of a label or a separate insert. Optionally, the kit may further comprise a standard or control information so that the test sample can be compared with the control information standard to determine whether a consistent result is achieved.

Examples

Generation of Mesodermally Differentiated hPSCs

Figure 1C:
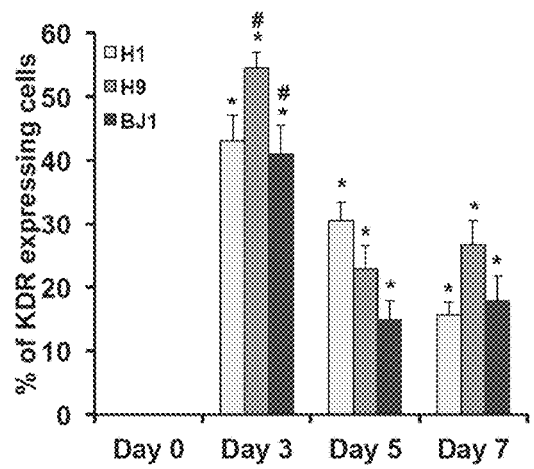
FIG. 1C shows data on flow cytometry analysis for KDR in three hPSC lines (H1, H9, or BJ1) cultured on collagen-coated plates with CHIR99021 treatment examined at indicated days.
Figure 1D:
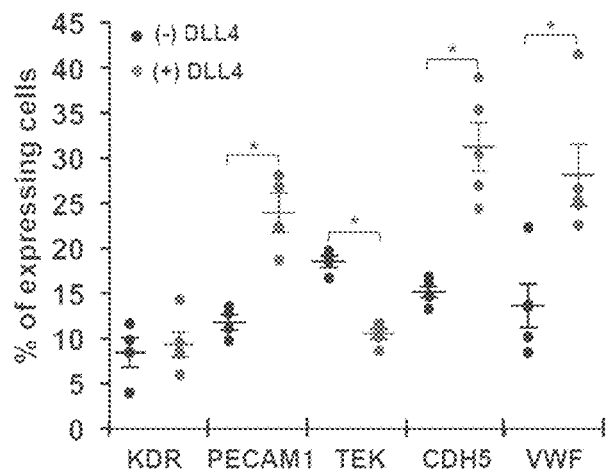
FIG. 1D shows data on flow cytometric analysis for EC-lineage markers in differentiating hESCs (H9) with or without DLL4 treatment determined at day 14.

A clinically compatible stepwise protocol was developed which follows endothelial development (FIG. 1A). To develop a fully defined system, KnockOut™ Serum Replacement substituted for animal serum and feeder cells. As a first step, two coating materials were compared (collagen and Matrigel™), and induced differentiation of hPSCs into the mesodermal lineage using CHIR99021, a GSK3β inhibitor which mimics Wnt activation. hESCs (H9) were plated onto dishes coated with 0.01% collagen or 10% Matrigel™ and were cultured for 3, 5, and 7 days in hESC medium with or without 3 M CHIR99021. Real-time RT-PCR (qRT-PCR) showed that T (also known as Brachyury) and KDR transcripts were most highly expressed in conditions using collagen coating and CHIR99021 treatment for 3 days (FIG. 1). The expression of definitive ectoderm (SOX1) and endoderm (FOXA2) markers were not significantly changed, and POU5F1 (OCT4) expression was reduced. Flow cytometry analyses confirmed that the percentage of KDR+ cells was highest (51.2±4.3%) under these conditions. Another hESC line (H1) and a hiPSC line (BJ1) showed similar results (FIG. 1C).

DLL4 Promotes EC Differentiation and Inhibits Hematopoietic Lineage Differentiation These mesodermally differentiated hPSCs were cultured in medium containing VEGFA, FGF2, EGF, DLL4, and heparin for 5-9 days from day 4. qRT-PCR showed new expression or substantial increase of KDR, PECAM1, TEK (TIE2), CDH5, and VWF at day 14 compared to undifferentiated hPSCs and mesodermally-differentiated hPSCs at day 3. Addition of a Notch ligand, DLL4, further increased KDR, PECAM1, CDH5 and VWF expression. Flow cytometric analyses also confirmed increases in PECAM1, CDH5, and VWF (FIG. 1D) and decreases in PTPRC (CD45), CD34, KIT (CD117), and PROM1 (CD133). These data imply that DLL4 promotes EC differentiation and inhibits hematopoietic lineage differentiation. Similar results were found in three hESC lines (H1, H7, and H9) and two hiPSC lines (BJ1 and PGP1) by flow cytometry and qRT-PCR. In double flow cytometry, 98.6% of CDH5+ cells expressed VWF, 79.0% TEK, and 66.3% KDR, suggesting substantial enrichment of the EC population in the CDH5+ cell fraction. Immunocytochemistry confirmed expression of EC markers VWF and CDH5 as well.

Nitric oxide (NO) production was demonstrated in these cells by a NO-sensitive fluorescent dye, 4-amino-5-methylamino-2', 7'-difluorofluorescein (DAF-FM) diacetate. When plated on Matrigel™, the cells formed vascular-like structures. These results indicate that a combination of angiogenic factors together with EGF and DLL4 efficiently induced endothelial differentiation of hPSCs.

Purification of hPSC-Derived ECs

Figure 1E:
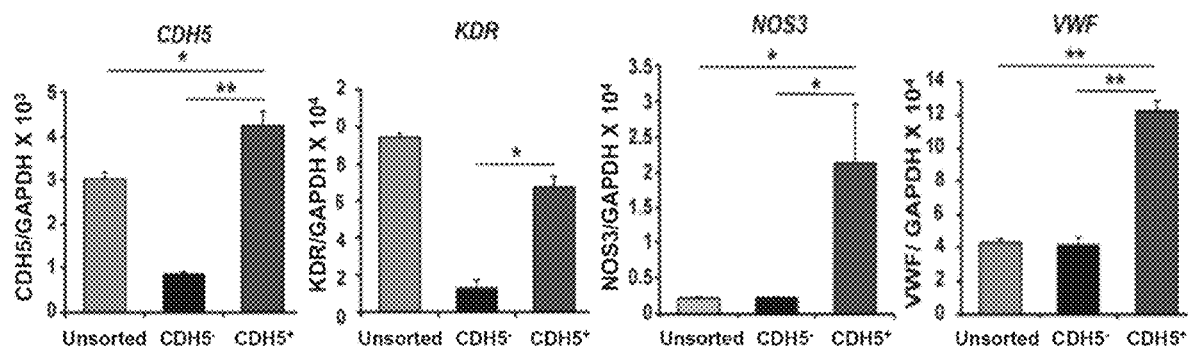
FIG. 1E shows data on mRNA expression of EC genes measured by qRT-PCR in endothelially differentiated hPSCs before and after sorting for CDH5 with MACS.

To enrich endothelial-lineage cells, the differentiated cells were sorted at day 14 for CDH5 with the magnetic-labeled cell separation system (MACS®). The sorted CDH5+ cells exhibited 3- to 8-fold higher mRNA expression of KDR, NOS3 (eNOS), and VWF compared to CDH5− cells (FIG. 1E). Immunocytochemistry demonstrated that almost all CDH5+ cells expressed VWF and CDH5. The hPSC-CDH5+ cells showed typical cobblestone-like EC morphology and produced NO detected by DAF-FM diacetate. These CDH5+ cells formed tubular structures in Matrigel and showed uptake of DiI acetylated-LDL and binding to UEA-1 lectin. In agreement with the in vitro results, co-localization of the injected cells were found with ILB4 positive vessels in vivo using a Matrigel plug assay. These data suggest that the sorted hPSC-CDH5+ cells are highly enriched functional endothelial-lineage cells.

Pro-Angiogenic Properties of hPSC-Derived ECs

Figure 2A:
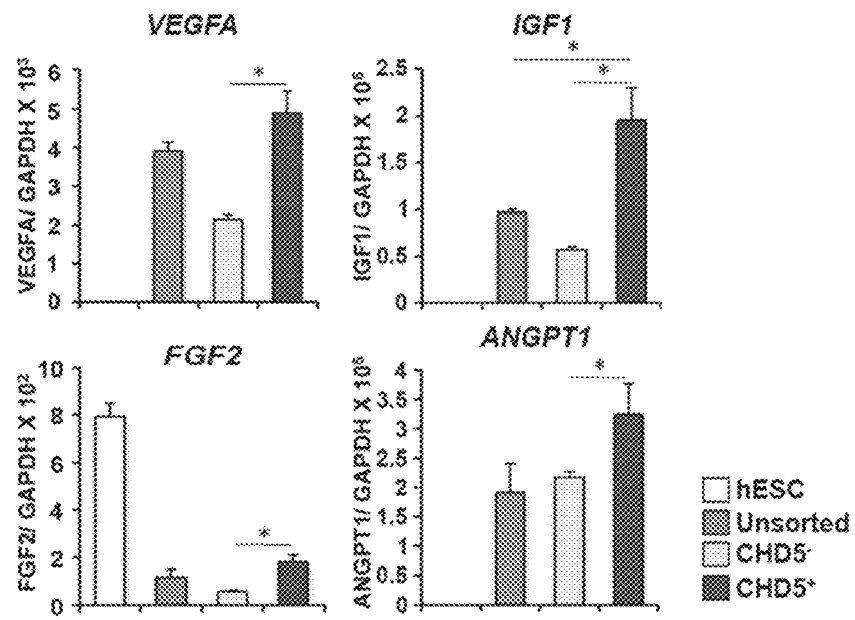
FIG. 2A shows data on mRNA expression of representative angiogenic factors in undifferentiated hPSCs, endothelially differentiated hPSCs before sorting at day 14, hPSC-CDH5-cells, and hPSC-CDH5+ cells measured by qRT-PCR. Data are presented as mRNA expression relative to GAPDH.
Figure 2B:
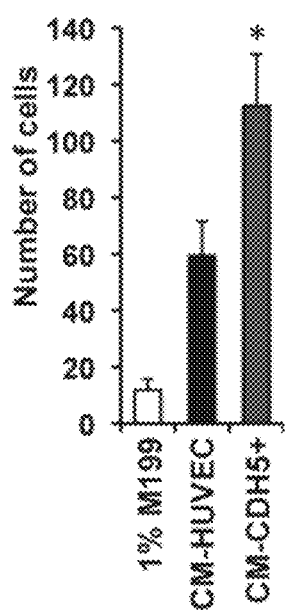
FIG. 2B shows data on migration. Sorted hPSC-CDH5+ cells and HUVECs were cultured in M199 media, and the conditioned media of CDH5+ cells (CM-CDH5+) and HUVECs (CM-HUVEC) were collected. M199 media containing 1% FBS was used as a negative control. Representative examples from are shown.
Figure 2C:
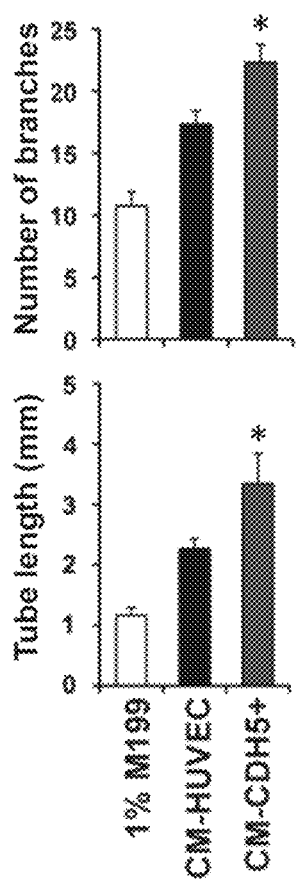
FIG. 2C shows data on tube formation assays.

To determine angiogenic activity of the sorted cells, expression of pro angiogenic factors were measured in pre- and post-sorted cells. qRT-PCR showed that mRNA expression of VEGFA, IGF1, ANGPT1, and FGF2 were significantly higher in the CDH5+ cells compared to the CDH5− cells or unsorted cells (FIG. 2A). Cell migration and tube-formation assays were conducted using conditioned media (CM) collected from cultured CDH5+ cells or HUVECs. In the cell migration assay with Boyden chamber, the number of migrated endothelial cells (ECs) was significantly higher in the CDH5+-cell group compared to the HUVEC group (FIG. 2B). For the tube formation assay, endothelial cells were cultured on Matrigel-coated plates and the above two conditioned media were added. Tube length and branches assessed 8 hours later were significantly higher in the CDH5+-CM-treated group compared to HUVEC-CM-treated group (FIG. 2C). These data indicate potent pro-angiogenic properties of hPSC-CDH5+ cells.

Figure 3A:
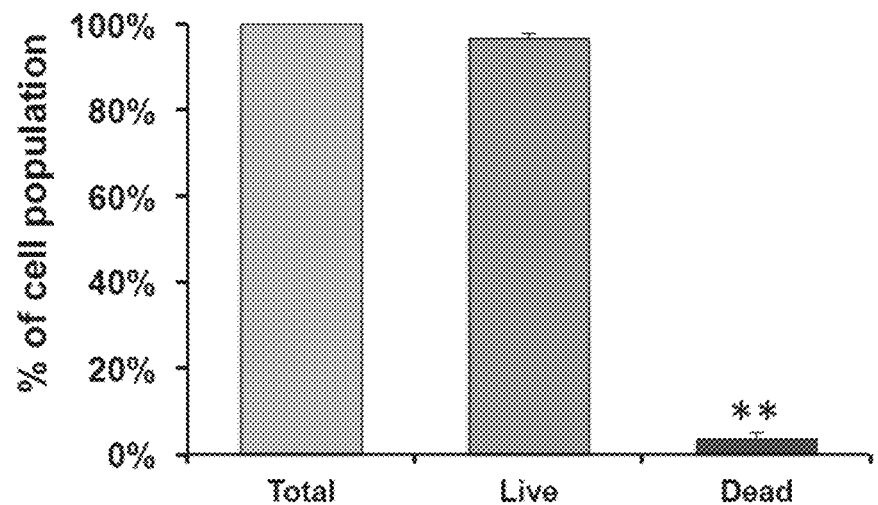
FIG. 3A shows data on cytoprotective effects of the nanomatrix gel encapsulation against H2O2. Quantification data derived from Live/Dead assay images of nanomatrix gel-encapsulated hPSC-ECs 7 days after culture in vitro.
Figure 3B:
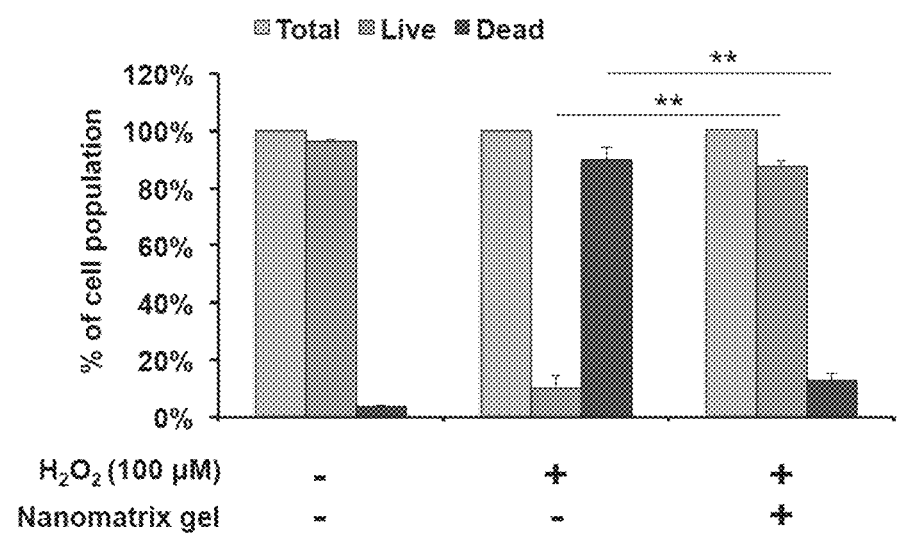
FIG. 3B shows data quantitative analysis of Live/Dead assay indicating encapsulation of hPSC-ECs within the nanomatrix gel increased cell survival after $H_2O_2$ (100 PM) treatment.

Cytoprotection of hPSC-ECs Under Oxidative Stress by the Nanomatrix Gel Encapsulation Whether peptide amphiphile, PA-RGDS, nanomatrix gel supports the viability of hPSC-derived ECs in regular culture conditions was examined. hPSC-derived ECs were encapsulated within the nanomatrix gel and cultured for 7 days under normal endothelial cell culture conditions. Live/Dead staining at day 7 demonstrated that 96.5±1.3% encapsulated hESC-ECs were viable (FIG. 3A). Whether hPSC-ECs can survive under oxidative stress, which is a major cause of low cell survival in ischemic tissues, was evaluated. hPSC-ECs encapsulated within the nanomatrix gel were exposed to a high concentration of $H_2O_2$ (100 M). Live/Dead staining demonstrated that viability was 8.2 times better when hPSC-ECs were encapsulated than not (FIG. 3B). These results indicate that encapsulation of hPSC-ECs within the nanomatrix gel can promote EC survival under oxidative stress.

Degradation Kinetics of the Nanomatrix Gel In Vivo

To examine the in vivo degradation of the nanomatrix gel, the gel was pre-labeled with CM-DiI, a red fluorescent dye. Hindlimb ischemia (HLI) was surgically induced in nude mice and the nanomatrix gel was implanted into the ischemic hindlimb. The mice were euthanized at 1, 3, or 6 weeks after injections, and the hindlimb tissues were harvested. Through histological evaluation under confocal microscopy, the DiI-labeled nanomatrix gel was gradually decreased in muscle tissue over time and was almost completely degraded at 6 weeks.

Figure 4A:
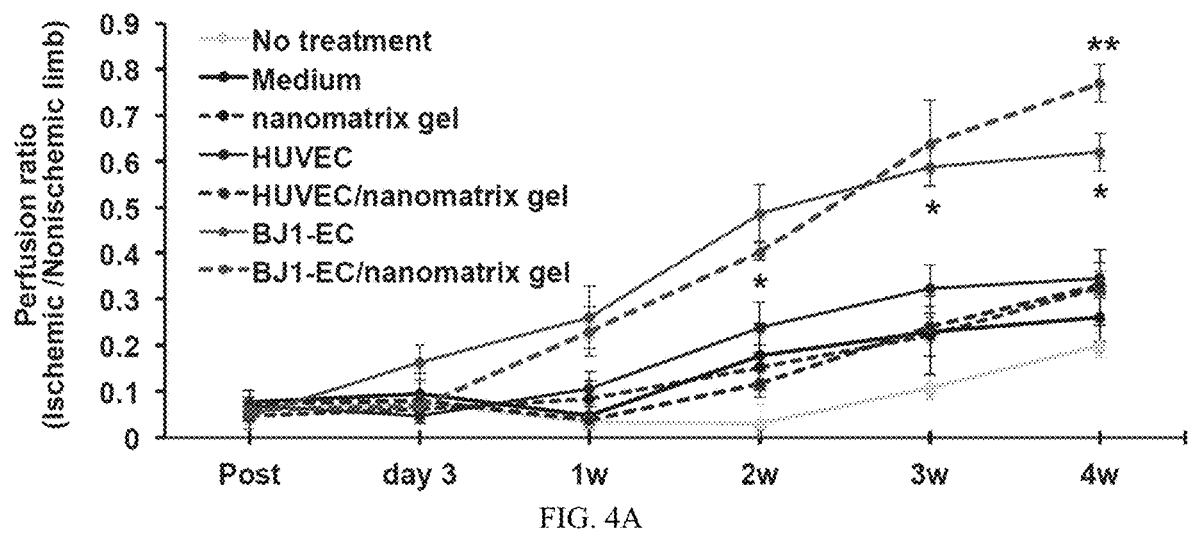
FIG. 4A shows quantitative analysis of blood flow in the mice receiving surgery only (No treatment), Medium, nanomatrix gel, HUVECs, HUVEC/nanomatrix gel, hPSC-EC, or hPSC-EC/nanomatrix gel over four weeks after treatment of hPSC-ECs encapsulated within the nanomatrix gel in hindlimb ischemia
Figure 4B:
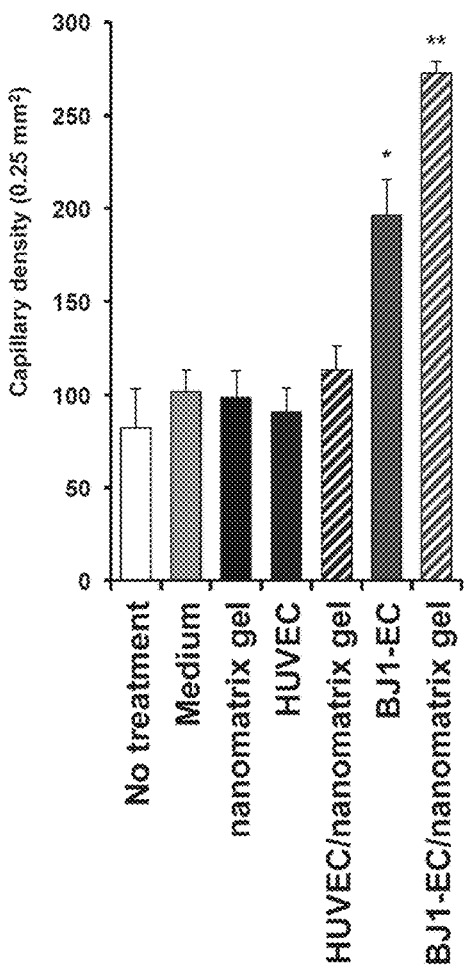
FIG. 4B shows data quantitative analysis of vascular density.

Therapeutic Effects of hPSC-ECs Encapsulated within the Nanomatrix Gel on Hindlimb Ischemia To determine the therapeutic effects of hPSC-derived ECs encapsulated within the nanomatrix gel on ischemic disease, a HLI model was used. HLI was surgically induced in nude mice and transplanted hPSC (BJ1-hiPSC) ECs ($2 \times 10^5$) encapsulated with or without the nanomatrix gel, HUVECs ($2 \times 10^5$) with or without the nanomatrix gel, the nanomatrix gel only, or culture medium into hindlimb muscle. The hPSC-EC group were compared to the other groups (except the encapsulated hPSC-EC group) by ANOVA. The encapsulated hPSC-EC group were compared to the bare hPSC-EC group by the t-test. Laser Doppler perfusion image (LDPI) analysis demonstrated that the hPSC-EC group showed higher blood flow compared to other groups such as no treatment (surgery only), medium, the nanomatrix gel only, and HUVECs with or without the nanomatrix gel (FIG. 4A). The hPSC214 EC/nanomatrix gel group showed higher blood flow than the bare hPSC-EC-group at 4 weeks. Similar experiments with another cell line, H9 hESCs, and resulted in similar data. Vascular density was determined in tissues harvested at 4 weeks which were systemically perfused with FITC-conjugated isolectin B4 (ILB4). The functional vascular density was again higher in the hPSC-EC group compared to the other groups when omitting the encapsulated hPSC-EC group. But when the encapsulated and bare hPSC-EC groups were compared, the vascular density was significantly higher in the encapsulated group (FIG. 4B). Taken together these results indicate that encapsulation of hPSC-ECs within the nanomatrix gel is most effective for repairing limb ischemia and augments functional neovascularization.

Prolonged Engraftment of hPSC-ECs Encapsulated within the Nanomatrix Gel in Ischemic Tissues Long-term temporospatial behavior of the implanted hPSC-ECs in ischemic disease models was examined. The fate of implanted cells by BLI was monitored over 21 weeks and histologically for 10 months. For BLI studies, hPSC-ECs were transduced with a reporter gene consisting Fluc-TdTomato (Fluc+TdTomato+hPSC-CDH5+) before transplantation. It was confirmed that >90% of the transduced hPSC-ECs expressed TdTomato by fluorescence microscopy and flow cytometry. The exposure time to detect bioluminescence signals was optimized after encapsulating hPSC-ECs within the nanomatrix gel. These conditions were used or in vivo BLI experiments. In mice receiving hPSC-ECs only, bioluminescence signals increased over 3 days, but dramatically reduced thereafter approaching an undetectable level at week 3. However, in mice receiving nanomatrix gel-encapsulated hPSC-ECs, the bioluminescence signals were gradually increased over one week, presumably because degradation of the nanomatrix gel over this period allowed quicker penetration of luciferin into the nanomatrix gel and hPSC-ECs. These BLI signals were well maintained between 2 and 14 weeks, but rapidly decreased to a minimally detectable level by 21 weeks. From one week and on, the BLI signals were consistently higher in the encapsulated group than in the non-encapsulated group.

Figure 5:
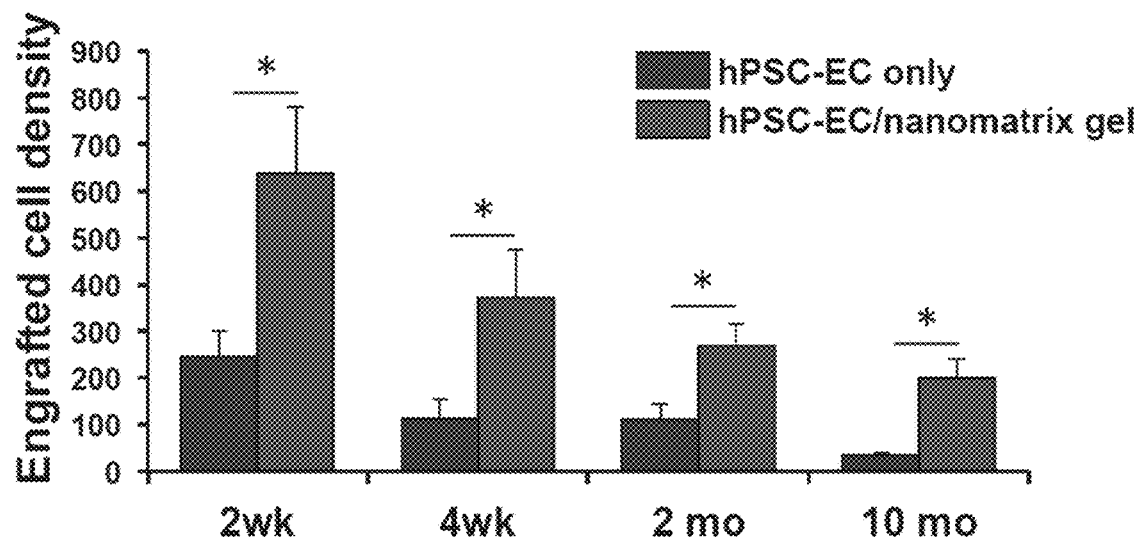
FIG. 5 shows data on quantification of engrafted cell density. Muscle sections were implanted with bare or nanomatrix gel-encapsulated hPSC-ECs from BJ1. Fluc+Tomato+hPSC-ECs, alone or encapsulated within nanomatrix gel, were transplanted into ischemic hindlimbs and were tracked noninvasively by BLI over 21 weeks.

For histological analysis, hPSC-ECs were pre-labeled with a red-fluorescent dye, DiI, and both nanomatrix gel-encapsulated and bare hPSC-ECs were transplanted into the hindlimb following HLI surgery. Muscle tissues were harvested at 2 weeks, 4 weeks, 2 months, and 10 months and performed immunohistochemistry. Confocal microscopic examination of the tissues demonstrated that the number of engrafted cells were gradually decreased over 10 months in both groups, but at all measured points it was significantly higher in the nanomatrix gel-encapsulated group compared to the bare hPSC-EC group (FIG. 5). Taken together, encapsulation of hPSC-derived ECs within the nanomatrix gel substantially increased engraftment and long-term survival of transplanted hPSC-ECs in ischemic hindlimbs.

In Vivo Neovascularization of Nanomatrix Gel-Encapsulated hPSC-ECs

To investigate angiogenic effects of hPSC-EC transplantation, qRT-PCR was performed with muscles harvested at 2 and 4 weeks. Expression of six representative angiogenic genes (Vegfa, Angpt1, Fgf2, Igf1, Ccl2 (Mcp-1), and Pdgfb) were compared between mice receiving the nanomatrix gel-encapsulated hPSC-ECs, hPSC-ECs, HUVECs, or the nanomatrix gel only. Expression (mRNA) was compared between the hPSC-EC group and control groups (HUVEC or nanomatrix gel). The hPSC-EC group showed higher expression of Vegfa and Angpt1 compared to the controls at 2 weeks and Mcp-1 at 4 weeks. Next, mRNA expression was compared between the nanomatrix gel-encapsulated hPSC-EC group and the bare hPSC-EC group. Both at 2 and 4 weeks, expression of all the genes except Angpt1 (2 weeks) and Ccl2 (4 weeks) was significantly higher in the encapsulated hPSC-EC group compared to bare hPSC-ECs. These data indicate that while bare hPSC-EC injection increased limited angiogenic and arteriogenic factors for 2 to 4 weeks, the encapsulated hPSC-ECs increased most representative angiogenic, arteriogenic, and cytoprotective factors more robustly and for longer than 4 weeks.

Figure 6A:
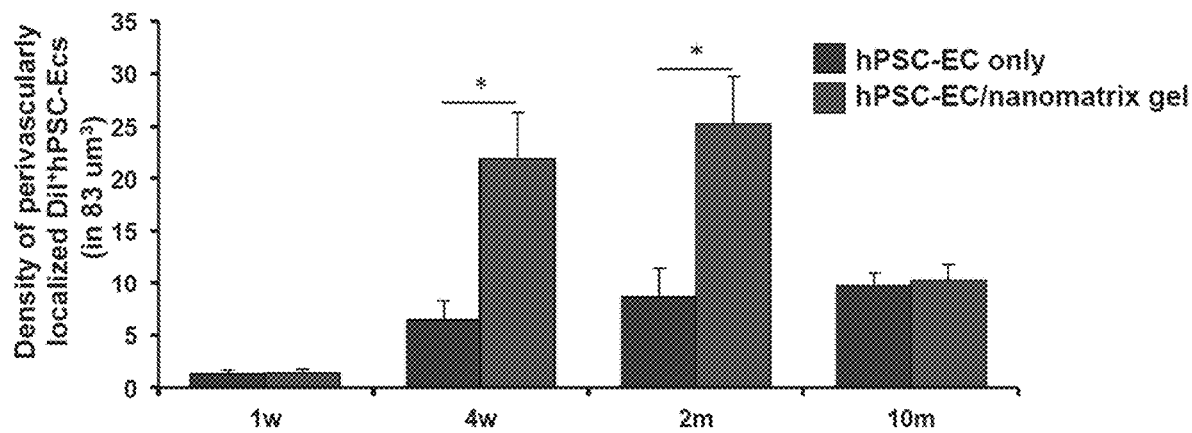
FIG. 6A shows data on the quantification of perivascularly localized hPSC-ECs per engrafted cells over time. Hindlimb tissues were implanted with nanomatrix gel only, HUVECs only, hPSC (BJ1)-ECs only, or encapsulated hPSC (BJ1)-ECs within the nanomatrix gel. Confocal microscopic images were taken at 1, 4 weeks, 2 months and 10 months after implantation of bare or nanomatrix gel-encapsulated DiI-labeled hPSC-ECs.
Figure 6B:
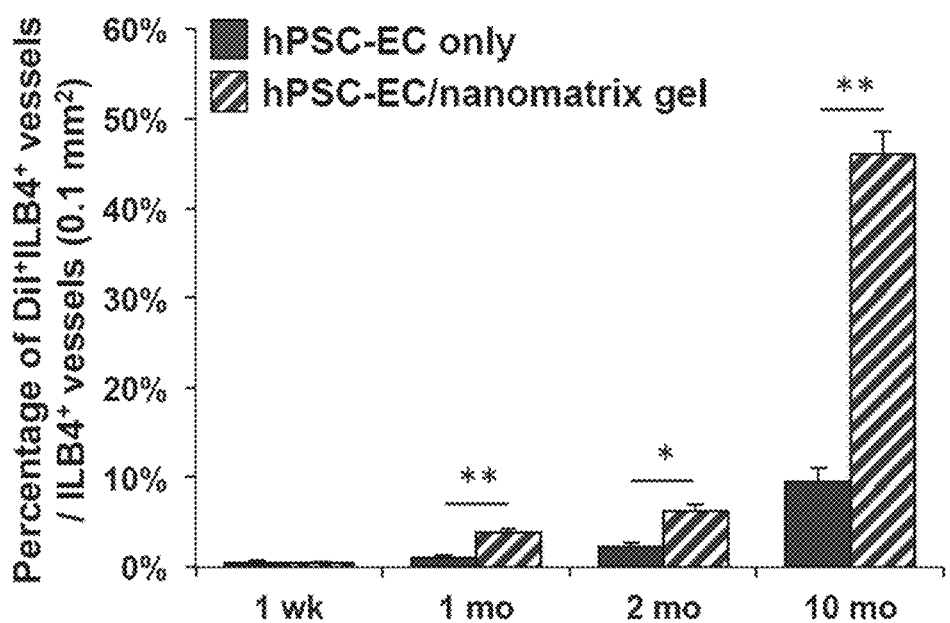
FIG. 6B shows data on the quantitative analysis showing the percentages of hPSC-ECs-incorporated vessels (DiI+ ILB4+) per total vessels (ILB4+).
Figure 6C:
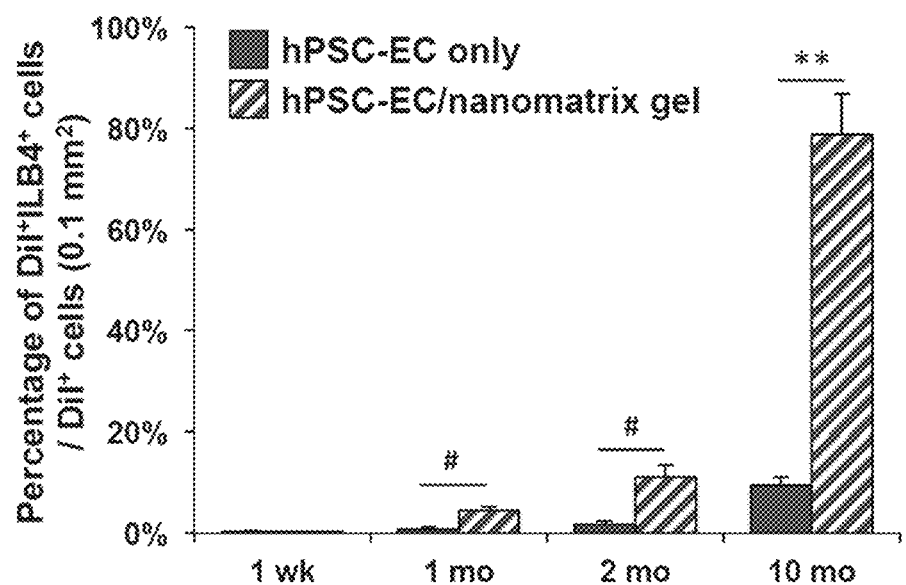
FIG. 6C shows data on intravascularly incorporated hPSC-ECs (DiI+ILB4+) per total engrafted hPSC-ECs (DiI+).

Vasculogenic effects or direct contribution of hPSC-ECs to vessel formation over 10 months was examined via histological analyses. For these experiments, FITC ILB4 was systemically injected before sacrifice to identify functional endothelium. Confocal microscopic examination of tissues demonstrated that engrafted hPSC-ECs were more frequently observed near the vasculature over time (FIG. 6b-d). Quantitatively, the proportion of perivascularly localized hPSC-ECs per total engrafted hPSC-ECs were gradually increased over time in both encapsulated and bare hPSC-EC injected groups; however, the absolute numbers were significantly higher in the encapsulated hPSC-EC group (FIG. 6A). Moreover, from 4 weeks to 10 months after implantation, some of the engrafted hPSC-ECs in both bare and encapsulated groups were linearly aligned, mimicking vascular structures, suggesting their guiding role for vascular growth during remodeling.

Temporal changes in incorporation of hPSC-ECs into the vessels were examined. In the unencapsulated hPSC-EC group, very few hPSC-ECs were incorporated into vessels at one week. However, the proportion of hPSC-EC-incorporated vessels (DiI+ILB4+) among total functional vessels (ILB4+) increased over time: less than 1% at 4 weeks and 9.4% at 10 months (FIG. 6B). In the nanomatrix gel encapsulated hPSC-EC group, the proportion was similarly low at 1 week; however, it progressively increased between 1 and 10 months and at each time point (1, 2, 10 months) it was significantly higher compared to the unencapsulated group (FIG. 6B). At 10 months, the proportion of hPSC-EC incorporated vessels reached 45.9%, and 78.6% of engrafted or remaining hPSC-ECs were completely incorporated into vessels (FIG. 6C). Notably, vessels incorporated with multiple hPSC-ECs were observed, which was rarely seen at other time points. Moreover, some of unincorporated hPSC-ECs were linearly or curvilinearly aligned like vessels parallel to or continuous with host vessels and a part of them were faintly stained positive for ILB4, indicating that hPSC-ECs play a guiding role for new vessel formation. Together, these data suggest that engrafted hPSC-ECs were initially moving toward vessels and gradually incorporated into vessels, and the nanomatrix gel, by enabling long-term cell survival, allowed sustained vasculogenic effects of hPSC-ECs.

Tissues were stained with endodermal marker AFP and ectodermal markers SOX1 and Nestin and did not detect cells differentiated into other lineages. Gross and microscopic examination showed no discernible tumors after injection with hPSC-ECs in 88 animals. Together, these data suggest that implantation of hPSC-ECs encapsulated with PA-RGDS recovered blood flow through enhancement of cell retention and neovascularization within ischemic hindlimb.

Human Pluripotent Stem Cell Culture and Differentiation

The hESCs (H1, H7, and H9) and hiPSCs (BJ1 and PGP1 obtained from Dr. George Daley) were cultured in mTeSR™ 1 (STEMCELL Technologies) on 5% matrigel at 37° C., 5% CO2. For directed differentiation, enzymatically dissociated clumps of hPSCs (lower than passage 60) were cultured on 0.01% collagen-coated plates in DMEMF-12 including 20% Serum Replacement (SR) with or without addition of specific differentiation factors for 7-10 days. hPSCs were cultured on collagen coated plates for an additional 14 days.

Magnetic Activated Cell Sorting (MACS)

For sorting of CDH5+ with MACS, differentiated hPSCs were incubated with APC-conjugated mouse anti-human CDH5/CD144 (17-1449-42, eBioscience). After washing, the cell pellet was incubated with anti-APC beads (120-001-265, Miltenyi Biotec) and subjected to MACS sorting (Miltenyi Biotec).

Fabrication of the Nanomatrix Gel

Two PAs, C16-GTAGLIGQRGDS (SEQ ID NO: 1) (PA-RGDS) and C16-GTAGLIGQS (SEQ ID NO: 3) (PA-S), were synthesized via Fmoc-chemistry using an Aapptec Apex peptide synthesizer. The peptides were then alkylated at the N-termini via two 12 h reactions with palmitic acid in the presence of a mixture of o-benzotriazole-N,N,N',N'-tetramethyluronium hexafluorophosphate (HBTU) and diisopropylethylamine (DiEA) dissolved in dimethylformamide (DMF). This was followed by cleavage from the resin and deprotection for 3 h, using a 40:1:1:1 cocktail of trifluoroacetic acid (TFA), deionized water, triisopropylsilane (TIPS), and anisole. The collected samples were subjected to rotary evaporation to remove excess TFA, precipitated in diethyl ether, and lyophilized. Successful synthesis of the PAs was confirmed via matrix-assisted laser desorption ionization time-of-flight (MALDI-TOF) mass spectrometry. Stock solutions of the 2 PAs, PA-RGDS and PA-S [2% (weight/volume)] were individually prepared by dissolving lyophilized PA in distilled water and adjusting the pH to 7 using 1M sodium hydroxide (NaOH). The two PA solutions were then mixed in a 1:1 molar ratio, and self-assembly into three-dimensional hydrogels was induced by combining 50 μL of PA solution with a mixture containing 15 L of 0.1 M CaCl2) and 25 μL of cell suspension.

The invention claimed is:

1. A method of producing pluripotent stem cell-derived endothelial cells comprising:
    culturing pluripotent stem cells in a serum free growth medium comprising serum replacement, a GSK3β inhibitor and fibroblast growth factor 2 (FGF2) on a coated surface, wherein the coating of the coated surface comprises collagen, under conditions such that the pluripotent stem cells express increased Brachyury (T) and vascular endothelial growth factor receptor 2 (KDR) transcripts providing mesodermally differentiated cells;
    culturing the mesodermally differentiated stem cells in a serum free growth medium comprising serum replacement, delta-like canonical notch ligand 4 (DLL4), fibroblast growth factor 2 (FGF2), and heparin in the absence of the GSK3β inhibitor under conditions such that the mesodermally differentiated stem cells express increased PECAM1, CDH5, and VWF transcripts providing pluripotent stem cell-derived endothelial cells,
    purifying the pluripotent stem cell-derived endothelial cells by selecting cells that express a CDH5 cell surface marker and wherein the pluripotent stem cell-derived endothelial cells produce nitric oxide; and
    culturing the selected cells in a serum free maintenance growth medium comprising serum replacement, vascular endothelial growth factor A (VEGFA), epidermal growth factor (EGF), heparin and FGF2, in the absence of exogenous DLL4.

2. The method of claim 1, wherein culturing pluripotent stem cells with a GSK3β inhibitor is on the coated surface for not more than 4 days.

3. The method of claim 1, wherein the pluripotent stem cells are embryonic stem cells or induced pluripotent stem cells.

4. The method of claim 1, wherein the GSK3β inhibitor is 6-[[2-[[4-(2,4-dichlorophenyl)-5-(5-methyl-1H-imidazol-2-yl)-2-pyrimidinyl]amino]ethyl]amino]-3-pyridinecarbonitrile (CHIR99021).

5. The method of claim 1, wherein
    the serum free growth medium for culturing pluripotent stem cells further comprises DMEM/F12.

6. The method of claim 1, wherein
    the serum free growth medium for culturing pluripotent stem cells and/or for culturing the mesodermally differentiated stem cells is in a mesodermal differentiation medium.

7. The method of claim 1, wherein the pluripotent stem cells are human embryonic stem cells.

8. The method of claim 1, wherein the pluripotent stem cells are human induced pluripotent stem cells.

9. The method of claim 1, wherein the GSK3β inhibitor is present in a concentration of 3 μM.

10. The method of claim 1, wherein FGF2 is present in a concentration of 4 ng/mL.

11. The method of claim 1, wherein DLL4 is present in a concentration of 25 ng/mL.

12. The method of claim 1, wherein heparin is present in a concentration of 5 u/mL.

13. The method of claim 1, wherein the serum-free growth medium for culturing the mesodermally differentiated stem cell further comprises epidermal growth factor (EGF).

14. The method of claim 13, wherein the EGF is present in an amount of 5 ng/mL.

15. The method of claim 1, wherein the serum-free growth medium for culturing the mesodermally differentiated stem cell further comprises vascular endothelial growth factor A (VEGFA).

16. The method of claim 15, wherein the VEGFA is present in an amount of 10 ng/mL.

17. The method of claim 1 further comprising:
    encapsulating the cultured selected pluripotent stem cell-derived endothelial cells within a nanomatrix gel comprising C16-GTAGLIGQRGDS (SEQ ID NO: 1) and C16-GTAGLIGQS (SEQ ID NO: 3).

* * * * *